(12) United States Patent
Yeo et al.

(10) Patent No.: US 9,341,502 B2
(45) Date of Patent: May 17, 2016

(54) ANALYSIS TOOL MEMBER

(71) Applicant: Presidium Instruments PTE LTD., Singapore (SG)

(72) Inventors: Joanne Yeo, Singapore (SG); Darren Koong, Singapore (SG); Reza Assadi, Singapore (SG)

(73) Assignee: Presidium Instruments Pte Ltd, Singapore (SG)

( * ) Notice: Subject to any disclaimer, the term of this patent is extended or adjusted under 35 U.S.C. 154(b) by 0 days.

(21) Appl. No.: 14/428,617

(22) PCT Filed: Sep. 12, 2013

(86) PCT No.: PCT/SG2013/000402
§ 371 (c)(1),
(2) Date: Mar. 16, 2015

(87) PCT Pub. No.: WO2014/042597
PCT Pub. Date: Mar. 20, 2014

(65) Prior Publication Data
US 2015/0233740 A1      Aug. 20, 2015

Related U.S. Application Data

(60) Provisional application No. 61/702,153, filed on Sep. 17, 2012.

(51) Int. Cl.
*G01D 21/00*    (2006.01)
*G01D 11/00*    (2006.01)
*G01N 33/00*    (2006.01)
*G01N 27/02*    (2006.01)
*G01N 25/18*    (2006.01)

(52) U.S. Cl.
CPC ............... *G01D 11/00* (2013.01); *G01N 25/18* (2013.01); *G01N 27/02* (2013.01); *G01N 33/00* (2013.01)

(58) Field of Classification Search
CPC .......... G01N 1/125; G01N 1/04; B63B 59/10
USPC ............... 73/866.5; 702/136; 324/72.5, 71.1
See application file for complete search history.

(56) References Cited

U.S. PATENT DOCUMENTS 4,151,462 A      4/1979   Teyler
4,860,753 A *   8/1989   Amerena ............... A61B 5/442
                                                                    324/690

(Continued)

OTHER PUBLICATIONS

International Search Report dated Dec. 5, 2013 and International Preliminary Report on Patentability dated Dec. 16, 2014 corresponding to PCT/SG2013/000402.

*Primary Examiner* — Lisa Caputo
*Assistant Examiner* — Nathaniel T Woodward
(74) *Attorney, Agent, or Firm* — Kilpatrick Townsend & Stockton LLP

(57) ABSTRACT

A detachable member and a processing member for an analysis tool, the detachable member including a housing for a probe member, the probe member capable of obtaining one or more characteristics information; and a circuitry component for co-operating with the member, the circuitry component including one or more electrical connections for transmitting one or more characteristics information to a separate processing member such that one or more characteristics information is capable of being used by the separate processing member for analysis.

25 Claims, 8 Drawing Sheets

(56) References Cited

U.S. PATENT DOCUMENTS

| | | |
|---|---|---|
| 5,124,645 A | 6/1992 | Rhoden et al. |
| 8,278,906 B2 * | 10/2012 | Loginov .................. B32B 15/08 324/693 |
| 2004/0061487 A1 | 4/2004 | Reasoner |
| 2005/0229698 A1 * | 10/2005 | Beecroft .................. G01J 3/02 73/300 |
| 2007/0257657 A1 | 11/2007 | Stevens et al. |
| 2012/0049836 A1 * | 3/2012 | Kessler .................. G01N 25/18 324/71.1 |
| 2012/0059619 A1 * | 3/2012 | Zhu ........................ G01N 25/18 702/136 |

* cited by examiner

502

(a)

(b)

ANALYSIS TOOL MEMBER

TECHNICAL FIELD

The present invention relates broadly to a detachable member for an analysis tool, to a processing member for an analysis tool; to a kit for an analysis tool and to a sensor holder for an analysis tool.

BACKGROUND

In the field of gemstone testing, characteristics such as electrical conductivity, thermal conductivity or thermal dissipation are typically used to facilitate in identification of gemstones. Gemstones can include diamonds, sapphire, moissanite, color stones etc. Various tools have been proposed for obtaining such characteristics. Some tools typically direct users to place gemstones in certain positions in a clamp member while the stones are irradiated or have currents passing through. However, due to differences in information obtained from different facets of gemstones, inaccurate readings may be obtained with such tools.

One tool that has been gaining in popularity in testing/analysis of gemstones is that of a fix-tip-based analyser/tester. The analyser/tester may be in the form of a pen-like tester or a tester utilising a testing probe. The analyser comprises a metal cylindrical tip that is used to contact a gemstone such that electrical conductivity, thermal conductivity etc. information can be obtained. For quick confirmation of readings, the tip can be used on different portions of the gemstone in relatively shorter periods of time.

However, it has been recognised that such tip-based analysers are susceptible to tip damage. For example, repeated usage of contacting the tip with gemstones which are hard in nature can bend or blunt or break the tip. Further, repeated heating or current conduction using the tip may result in widening tolerance levels in readings. Such occurrences may give rise to problems because the tip is typically the main sensor on which the accuracy of the analyser device depends on. For damaged tips, a user is typically asked to return the tool to the manufacturer for manual replacement of the tip and calibration. This can result in downtime for the user, as well as increased costs e.g. for transportation/shipping, for repairs etc. In addition, the manufacturers may have to devote a section of facilities to deal with such tool repairs and devote expertise in electrical connections and calibrations.

It will further be appreciated that the above problems may also exist for other fields that use tip-based analysis equipment.

Therefore, there exists a need for a detachable member for an analysis tool, a processing member for an analysis tool; a kit for an analysis tool and a sensor holder for an analysis tool that seek to address at least one of the above problems.

SUMMARY

In accordance with an aspect, there is provided a detachable member for an analysis tool, the member comprising a housing for a probe member, said probe member capable of obtaining one or more characteristics information; a circuitry component for co-operating with said member, the circuitry component comprising one or more electrical connections for transmitting said one or more characteristics information to a separate processing member such that said one or more characteristics information is capable of being used by the separate processing member for analysis.

The member may further comprise a mating part for detachably coupling the detachable member to the separate processing member.

The probe member may be capable of being used with an object under test, said object comprising a gemstone.

The circuitry component may be capable of being electrically coupled to the probe member, said probe member may be being configured at one contact end for analysis.

The circuitry component may comprise one or more contact pads for said transmission to the separate processing member.

The circuitry component may be configured to be in electrical communication with one or more connection members of the separate processing member.

The one or more connection members may comprise a spring means.

The probe member may comprise a cylindrical rod.

The cylindrical rod may comprise one or more biasing members for providing a spring action upon contact.

Said one or more characteristics information may comprise electrical information, thermal information or both.

The member may further comprise a base cover for exposing said one or more electrical connections, wherein the base cover may be configured to maintain the housing and the circuitry component within the detachable member.

The member may further comprise a usage sensor configured to inform a user on replacement of the elongated member.

The member may further comprise a calibration module for enabling calibration of the elongated member.

In accordance with another aspect, there is provided a processing member for an analysis tool, the processing member comprising a mating part to detachably couple the processing member to a detachable member for the analysis tool; a connector portion for receiving one or more characteristics information obtained at the detachable member, the connector portion being arranged to be in electrical communication with a processing module for analysis of said one or more characteristics information.

The processing member may be capable of being used with an object under test, said object comprising a gemstone.

The connector portion may comprise connection members for electrical connection to the detachable member.

The connection members may comprise spring-loaded pins.

Said one or more characteristics information may comprise electrical information, thermal information or both.

The processing member may further comprise an inner cover for exposing one or more connection points of the connector portion, wherein the inner cover may be configured to maintain the connector portion within the processing member.

The processing member may further comprise a usage sensor configured to inform a user on replacement of the detachable member.

The processing member may further comprise a calibration member for enabling calibration of the detachable member and/or the processing member.

In accordance with another aspect, there is provided a kit for an analysis tool, the kit comprising a detachable member as described above; and a processing member as described above.

In accordance with yet another aspect, there is provided a method of analysing an object, the method comprising providing a detachable member as described above; providing a processing member as described above; and detachably coupling the detachable member and the processing member.

In accordance with a further aspect, there is provided a sensor holder for an analysis tool, the holder comprising a housing for a probe member, said probe member capable of obtaining one or more characteristics information; one or more electrical connections provided for electrically coupling to the probe member; said one or more electrical connections further arranged to electrically couple to a circuitry component of the analysis tool; wherein transmission of said one or more characteristics information to a separate processing member, separate from the tip sensor holder, is capable of being performed via said one or more electrical connections.

BRIEF DESCRIPTION OF THE DRAWINGS

Example embodiments of the invention will be better understood and readily apparent to one of ordinary skill in the art from the following written description, by way of example only, and in conjunction with the drawings, in which.

DETAILED DESCRIPTION

Figure 1:
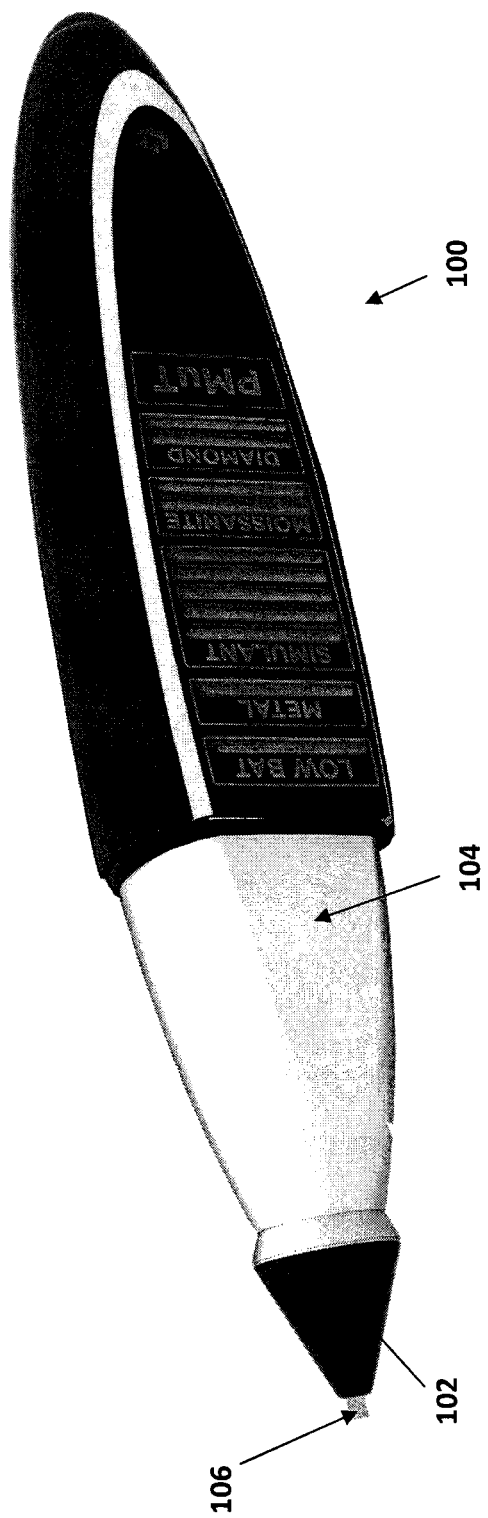
FIG. 1 is a schematic perspective view of an analysis tool in an example embodiment.

Example embodiments described herein can provide an analysis tool that comprises a detachable member that is removably attached to a main processing member. The detachable member can comprise a tip sensor and a removable sensor holder. Replacement of the tip sensor can be carried out by removing the detachable member. Preferably, the tip sensor can be removed from the detachable member.

The terms "coupled" or "connected" as used in this description are intended to cover both directly connected or connected through one or more intermediate means, unless otherwise stated.

The description herein may be, in certain portions, explicitly or implicitly described as algorithms and/or functional operations that operate on data within a computer memory or an electronic circuit. These algorithmic descriptions and/or functional operations are usually used by those skilled in the information/data processing arts for efficient description. An algorithm is generally relating to a self-consistent sequence of steps leading to a desired result. The algorithmic steps can include physical manipulations of physical quantities, such as electrical, magnetic or optical signals capable of being stored, transmitted, transferred, combined, compared, and otherwise manipulated.

Further, unless specifically stated otherwise, and would ordinarily be apparent from the following, a person skilled in the art will appreciate that throughout the present specification, discussions utilizing terms such as "scanning", "calculating", "determining", "replacing", "generating", "initializing", "outputting", and the like, refer to action and processes of an instructing processor/computer system, or similar electronic circuit/device/component, that manipulates/processes and transforms data represented as physical quantities within the described system into other data similarly represented as physical quantities within the system or other information storage, transmission or display devices etc.

The description also discloses relevant device/apparatus for performing the steps of the described methods. Such apparatus may be specifically constructed for the purposes of the methods, or may comprise a general purpose computer/processor or other device selectively activated or reconfigured by a computer program stored in a storage member. The algorithms and displays described herein are not inherently related to any particular computer or other apparatus. It is understood that general purpose devices/machines may be used in accordance with the teachings herein. Alternatively, the construction of a specialized device/apparatus to perform the method steps may be desired.

In addition, it is submitted that the description also implicitly covers a computer program, in that it would be clear that the steps of the methods described herein may be put into effect by computer code. It will be appreciated that a large variety of programming languages and coding can be used to implement the teachings of the description herein. Moreover, the computer program if applicable is not limited to any particular control flow and can use different control flows without departing from the scope of the invention.

Furthermore, one or more of the steps of the computer program if applicable may be performed in parallel and/or sequentially. Such a computer program if applicable may be stored on any computer readable medium. The computer readable medium may include storage devices such as magnetic or optical disks, memory chips, or other storage devices suitable for interfacing with a suitable reader/general purpose computer. In such instances, the computer readable storage medium is non-transitory. Such storage medium also covers all computer-readable media e.g. medium that stores data only for short periods of time and/or only in the presence of power, such as register memory, processor cache and Random Access Memory (RAM) and the like. The computer readable medium may even include a wired medium such as exemplified in the Internet system, or wireless medium such as exemplified in bluetooth technology. The computer program when loaded and executed on a suitable reader effectively results in an apparatus that can implement the steps of the described methods.

The example embodiments may also be implemented as hardware modules. A module is a functional hardware unit designed for use with other components or modules. For example, a module may be implemented using digital or discrete electronic components, or it can form a portion of an entire electronic circuit such as an Application Specific Integrated Circuit (ASIC). A person skilled in the art will understand that the example embodiments can also be implemented as a combination of hardware and software modules.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4% 2% to 3% etc., as well as individually, values within that range such as 1%, 2%, 3%, 4% and 5%. The intention of the above specific disclosure is applicable to any depth/breadth of a range.

FIG. 1 is a schematic perspective view of an analysis tool in an example embodiment. The analysis tool 100 comprises a detachable tip/head member 102 and a processing member 104. The processing member 104 is shown coupled to the detachable member 102. The analysis tool 100 further comprises a probe member such as an elongated member 106 for contacting an object under test. The elongated member 106 can be a cylindrical tip sensor that is preferably metallic. In addition, the processing member 104 may comprise a calibration port (not shown). The calibration port can allow calibration of the elongated member 106 via the processing member 104. The calibration port can allow various calibration methods such as calibration via wired connections, wireless connections etc. The wired connections can include, but are not limited to, universal serial bus connections, data port-type connections etc. The wireless connections can include, but are not limited to, bluetooth connections, WiFi connections, firewire connections etc.

In the example embodiment, the analysis tool 100 is a stand-alone hand-held tool. That is, the analysis tool 100 is not constrained in operation by e.g. connection to a desktop processing machine or tool. In the example embodiment, the analysis tool 100 is preferably used in a cableless configuration during operation. In the description, cableless is taken to include a connection that is without the use of wires or cables extending from the analysis tool 100 to any other machine/tool. The analysis tool 100 comprises a power source (not shown) within the processing member 104. The power source may be, for example, one or more rechargeable batteries and/or disposable energy sources. The analysis tool 100 can thus be portable to a user. By portable, it is meant, among other things, that the analysis tool 100 is capable of being transported relatively easily. Preferably, the analysis tool 100 may be carried in a pocket or palm-sized pouch. Therefore, the analysis tool can be more convenient over desktop setups for analysis.

In the example embodiment, the object under test may comprise a gemstone. The processing member 104 may preferably comprise different indicators on its body, such as light or mechanical flag indicators, for showing, for example, battery conditions, detection of metal content, detection of different levels of simulants, detection of diamond characteristics, detection of moissanite characteristics etc.

Figure 2:
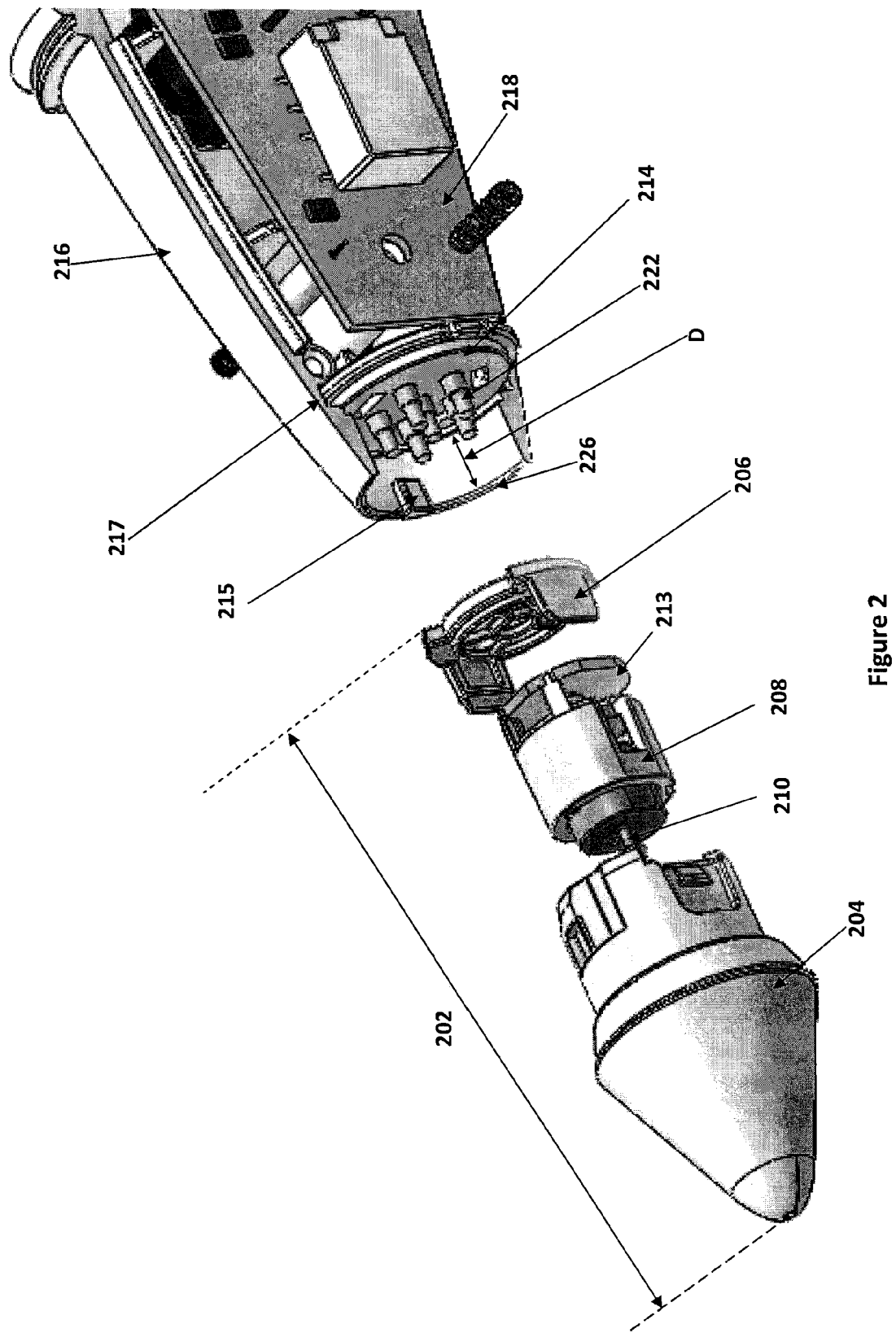
FIG. 2 is a schematic exploded partial drawing illustrating components of a detachable member and a processing member of an analysis tool in an example embodiment.

FIG. 2 is a schematic exploded partial drawing illustrating components of a detachable member 202 and a processing member 216 of an analysis tool in an example embodiment. The detachable member 202 and the processing member 216 are substantially similar to the detachable member 102 and the processing member 104 respectively as described with reference to FIG. 1. The detachable member 202 comprises a housing/casing or a tip portion 204, and a tip portion base cover 206. Within the housing or the tip portion 204, a tip sensor holder 208 is provided that is capable of securing/holding a probe member such as an elongated member 210 against the tip portion 204. The elongated member 210 is a tip sensor in the example embodiment. The tip sensor holder 208 is coupled to a tip portion circuitry component 213 disposed abutting the tip portion base cover 206. In the example embodiment, the circuitry component 213 is in the form of a printed circuit board. In the example embodiment, the tip sensor holder 208 may further comprise a resilient member (not shown) such as a spring. The usage of a spring may provide a relatively constant pressure applied at the elongated member 210. In addition, a spring may provide a suitable comfort level during contact of the elongated member 210 with a subject under test. Electrical connections can be provided from the elongated member 210 to the circuitry component 213 by the use of, for example but not limited to, one or more wires, passing through the tip sensor holder 208 and connecting to, e.g. contact pads of the circuitry component 213.

The tip portion base cover 206 and the tip portion 204 are provided with mating components such as mating grooves and protrusions in order to interlock and maintain the various components within the tip portion 204. In the example embodiment, the tip portion 204 is further configured, at the periphery external the tip portion base cover 206, to interlock, and engage the processing member 216. Thus, the tip portion base cover 206 is within the inner surface of the processing member 216. Such engagement can be e.g. via mating components such as mating grooves and protrusions. For example, mating members e.g. 215 of the processing member 216 may be used to interlock with the tip portion 204. This can detachably or removably couple the detachable member 202 to the processing member 216.

For the processing member 216, an inner case cover 214 of the processing member 216 is provided in a recessed groove 217 of the processing member 216. The recessed groove 217 may be provided at a distance D from the flange or lip of member 216. The inner case cover 214 is the top surface of the processing member 216 seen from the external of the processing member 216. Connection members e.g. 222 are provided projecting from the top surface of the inner case cover 214. The processing member 216 further comprises a processing module 218 that is electrically coupled to, or is in electrical communication with, the connection members e.g. 222. e.g. by wires hard-soldered to solder pads (not shown) of the processing module 218. The wires are in turn being e.g. hard-soldered to solder pads or leads of the connection members e.g. 222.

In the example embodiment, there are a number of electrical connections, for example six connections, to be connected from the elongated member 210 to the respective solder pads of the processing module 218. It will be appreciated that the number of electrical connections can vary based on the functions and/or number of components provided on the circuitry component 213. For example, an electrical signal may be sampled to determine the type or nature of the elongated member 210.

The connections beginning with the elongated member 210 can be electrical couplings to, or be in electrical communication with, the tip portion printed circuit board 213. These may be e.g. by wires from the elongated member 210 hard-soldered to solder pads provided on a top surface of the tip portion printed circuit board 213. The solder pads may be provided to be in electrical communication with contact pads provided on a bottom surface of the tip portion printed circuit board 213 via internal connections of the circuit board. The contact pads on the bottom surface are aligned with openings provided in the tip portion base cover 206 such that the contact pads are exposed for connection with the connection members e.g. 222 of the processing member 216.

That is, in the example embodiment, the inner case cover 214 is provided with openings and a connector portion (not shown) is aligned with the inner case cover 214 such that the connection members e.g. 222 are exposed for connection with the bottom surface of the tip portion printed circuit board 213, upon alignment with the openings of the tip portion base cover 206. In the example embodiment, the connection members e.g. 222 are preferably within the recessed depth of the processing member 216 such that they do not protrude beyond the lip 226 of the processing member 216.

Therefore, in the example embodiment, the detachable member 202 can be detachably coupled to the processing member 216. This can advantageously provide a relative quick and cheaper solution to tedious replacement of tips as present in the background art.

The inventors have also recognised that it may be difficult to electrically couple a plurality of signals (e.g. six or more connections) between the elongated member 210 and the processing member 216, given that the space in the tip housing 204 is typically constrained and limited. Further, it may also be costly to provide conventional electrical couplings.

In the example embodiment, the inventors have recognised that the connection members e.g. 222 can preferably be in the form of, but not limited to, spring-loaded pins e.g. so-called pogo pins. The inventors have recognised that pogo pins can be effectively utilised in the constrained and limited space due to their sizes. Further, pogo pins can be relatively cost effective and can provide elegant designs.

Preferably, connection between the detachable member 202 and the processing member 216 is in a cableless configuration.

As an example, the internal diameter of the tip housing is about 9.4 mm. The diameter of the printed circuit board 213 is about 9 mm. Contact pads on a bottom surface of the printed circuit board 213 are about 1 mm×2.3 mm in diameter (e.g. oval in shape). In addition, the diameter of each pogo pin is about 1.5 mm in diameter and each pogo pin has a height of about 7 mm. The diameter of the inner case cover 214 is about 15 mm while the solder pads e.g. 224 of the processing module 218 are about 1.5 mm in diameter.

In the following description, various described components are further described with exemplary details.

Figure 3:
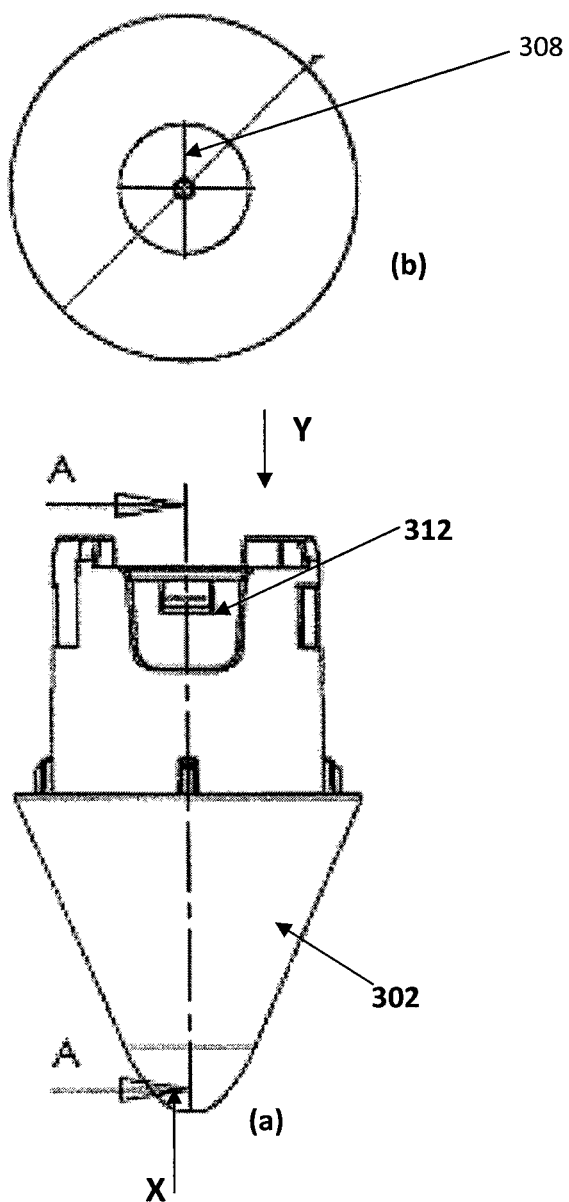
FIG. 3(a) is a side view of a tip portion in an example embodiment.
FIG. 3(b) is a bottom view of the tip portion when viewed in direction X.

FIGS. 3(a) and (b) are schematic drawings illustrating a tip portion in an example embodiment. The tip portion 302 is substantially identical to the tip portion 204 (FIG. 2). FIG. 3(a) is a side view of the tip portion 302; and FIG. 3(b) is a bottom view of the tip portion 302 when viewed in direction X.

The tip portion 302 comprises mating protrusions (not shown) for engaging and interlocking with corresponding recesses (compare 215 (FIG. 2)) of a processing member (not shown). A housing void (not shown) is provided within the tip portion 302 such that an elongated member (not shown) can extend from the void and emerge from an opening 308.

In addition, the tip portion 302 comprises mating catches e.g. 312 for engaging and interlocking with corresponding catches of a tip portion base cover (not shown) to retain components within the housing or tip portion 302.

Figure 4:
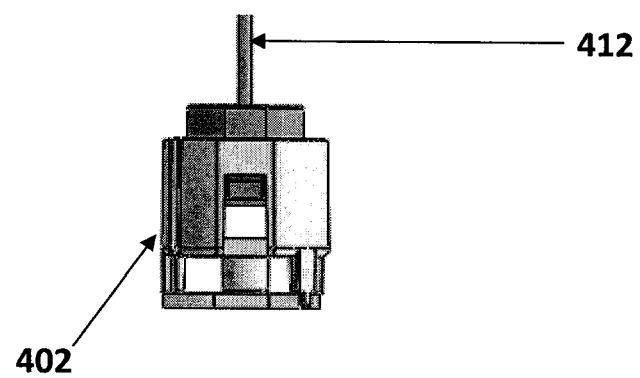
FIG. 4 is a side view of a tip sensor holder in an example embodiment.

FIG. 4 is a schematic drawing illustrating a tip sensor holder in an example embodiment. The tip sensor holder 402 is substantially identical to the tip sensor holder 208 (FIG. 2). FIG. 4 is a side view of the tip sensor holder 402.

The tip sensor holder 402 comprises a recess (not shown) for securing/holding a probe member such as an elongated member (not shown). An aperture or hole (not shown) may be provided for electrical connections e.g. wires to pass through. A probe member 412 is disposed and projecting from a top surface of the tip sensor holder 402. Optionally, additional structural members may be provided on the holder 402 to minimise the likelihood of short circuiting connections on an abutment e.g. a tip portion circuitry component (compare 213 (FIG. 2)).

Figure 5:
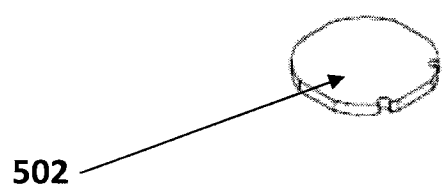
FIG. 5 is a perspective view of a tip portion printed circuit board in an example embodiment.

FIG. 5 is a schematic perspective view drawing illustrating a tip portion circuitry component in an example embodiment. The tip portion circuitry component is in the form of a printed circuit board 502 that is substantially identical to the tip portion printed circuit board 213 (FIG. 2).

Connections from a probe member such as an elongated member (not shown) can be electrical couplings to, or be in electrical communication with, the tip portion printed circuit board 502. The tip portion printed circuit board 502 may comprise solder pads (not shown) provided on a top surface of the tip portion printed circuit board 502 to allow e.g. wires from the elongated member to be hard-soldered to the solder pads. The solder pads are provided to be in electrical communication with contact pads (not shown) provided on a bottom surface of the tip portion printed circuit board 502. The contact pads (not shown) may be arranged in any suitable manner or pattern on the bottom surface of the tip portion printed circuit board 502. The solder pads are electrically connected to the contact pads via internal connections of the circuit board 502.

The contact pads are preferably arranged with one contact pad in substantially centre of the tip portion printed circuit board 502. Such arrangement optimally can facilitate incoming connections from connection members of a processing member. The arrangement of the contact pads can be aligned to openings provided in a tip portion base cover of a detachable member.

Figure 6:
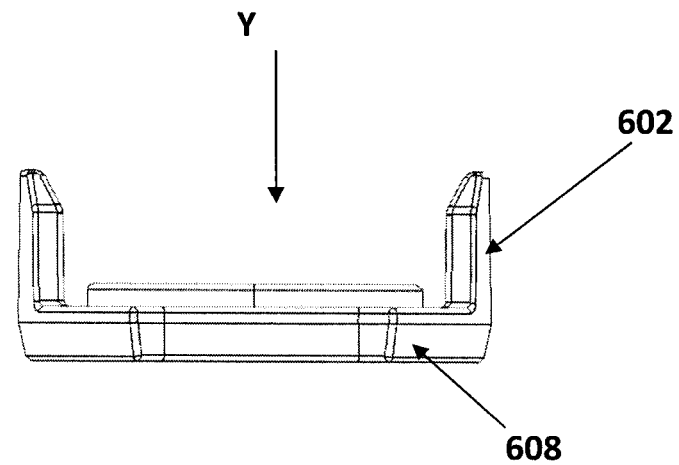
FIG. 6(a) is a side view of a tip portion base cover in an example embodiment.
FIG. 6(b) is a top view of the tip portion base cover when viewed from direction Y.
Figure 6:
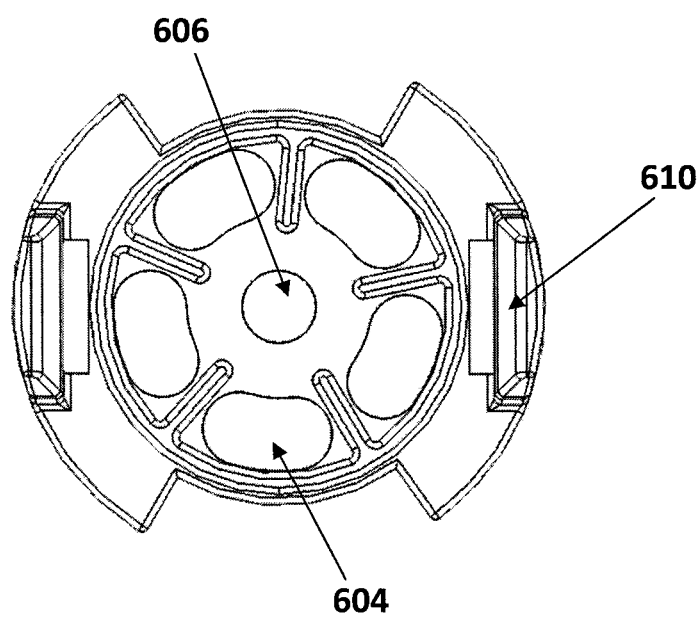

FIGS. 6(a) and (b) are schematic drawings illustrating a tip portion base cover in an example embodiment. The tip portion base cover 602 is substantially identical to the tip portion base cover 206 (FIG. 2). FIG. 6(a) is a side view of the tip portion base cover 602; and FIG. 6(b) is a top view of the tip portion base cover 602 when viewed from direction Y.

The tip portion base cover 602 comprises openings e.g. 604, 606 arranged on a base plate 608. The tip portion base cover 602 further comprises mating catches e.g. 610 for engaging and interlocking with corresponding catches (compare 312 (FIG. 3(a))) of a tip portion (not shown).

In the example embodiment, the arrangement of the openings e.g. 604, 606 can be aligned to contact pads (compare e.g. 508, 510 (FIG. 5(c))) provided on a bottom surface of a tip portion printed circuit board (not shown). The openings e.g. 604, 606 can be aligned with the contact pads (compare e.g. 508, 510 (FIG. 5(c))) such that the contact pads are exposed for connection with connection members of a processing member (not shown).

Figure 7:
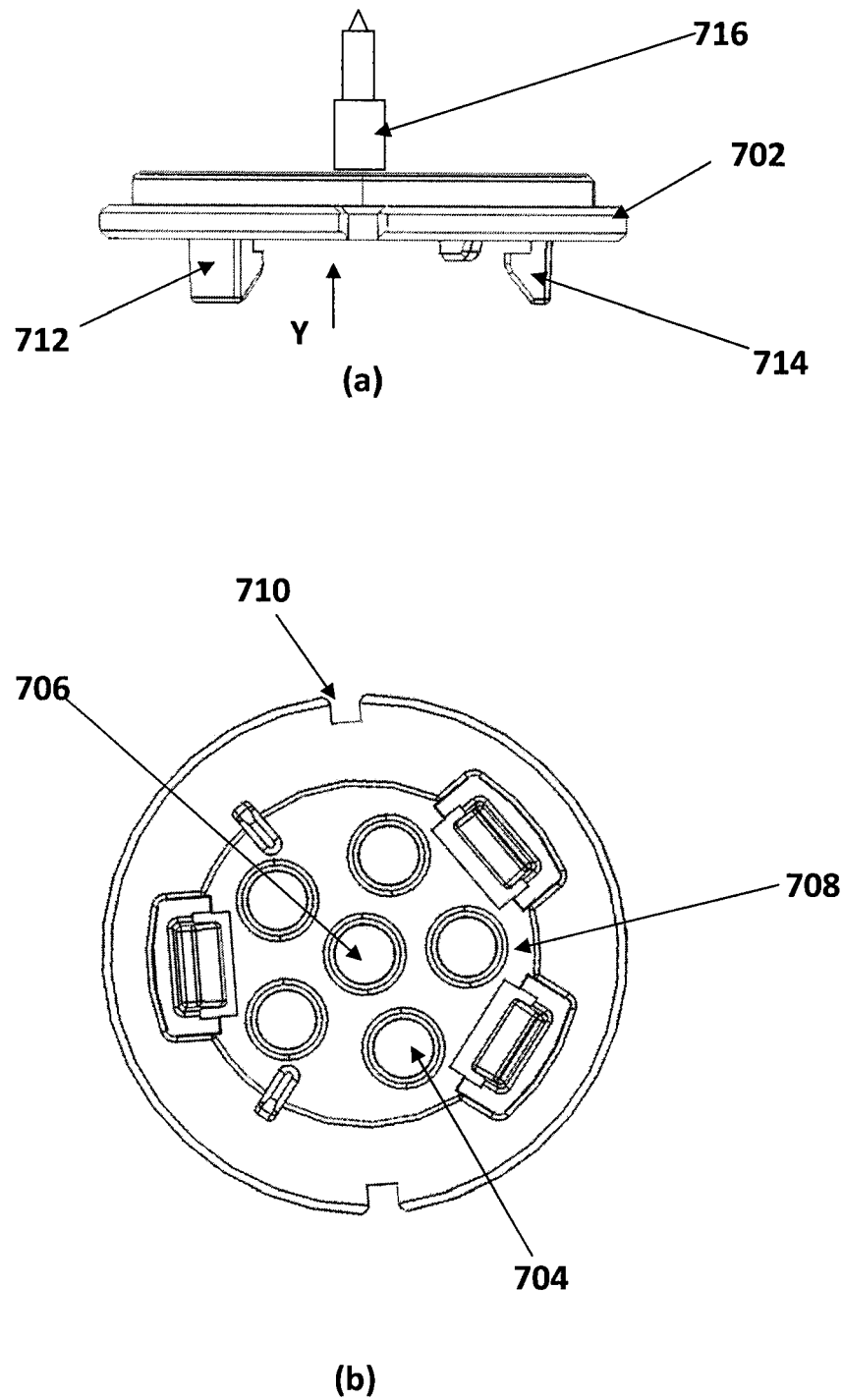
FIG. 7(a) is a side view of an inner case cover in an example embodiment.
FIG. 7(b) is a bottom view of the inner case cover when viewed from direction Y.

FIGS. 7(a) and (b) are schematic drawings illustrating an inner case cover in an example embodiment. The inner case cover 702 is substantially identical to the inner case cover 214 (FIG. 2). FIG. 7(a) is a side view of the inner case cover 702; and FIG. 7(b) is a bottom view of the inner case cover 702 when viewed from direction Y.

The inner case cover 702 comprises openings e.g. 704, 706 arranged on a base plate 708. The inner case cover 702 further comprises mating members e.g. 710 for engaging and interlocking with corresponding members of a recessed groove of a processing member (not shown) to retain the inner case cover 702 within the processing member. The positioning of the mating members e.g. 710 also facilitate the positioning and fitting of the inner case cover 702 into a processing member (compare 216 (FIG. 2)). The positioning of the various components of FIGS. 3 to 7 can ensure that the electrical connections from the elongated member are correctly coupled to corresponding contact points (compare 224 (FIG. 2)) of the processing member (compare 216 (FIG. 2)).

The inner case cover 702 further comprises, on a bottom surface, side walls e.g. 712, 714. Such side walls may guide connection members in the form of pogo pins (shown exemplarily as e.g. 716) to project from the top surface of the inner case cover 702. The pogo pins e.g. 716 may comprise leads for electrical connections to corresponding contact points of a processing member (not shown). A printed circuit board may optionally be provided for retaining such leads.

In the example embodiment, the arrangement of the openings e.g. 704, 706 may be aligned to contact pads (compare e.g. 508, 510 (FIG. 5(c))) provided on a bottom surface of a tip portion circuitry component or printed circuit board (not shown) and openings (compare e.g. 604, 606 (FIG. 6(b))) of a tip portion base cover of a detachable member, such that the contact pads of a detachable member are aligned for connection with the connection members of the connector portion of a processing member.

In an exemplary embodiment, a tip sensor with an analysis tool may be used with an object under test. The tip sensor can be brought into close proximity or contact with the object under test. The tip sensor may be in the form of an elongated member. Temperature changes for the object under test can be sensed via the tip sensor. For example, a heater element and a thermocouple may be disposed within the analysis tool with the tip sensor. The tip sensor can be heated and used to transmit heat to the object under test, and also to sense temperature change at the object under test. A thermistor may also be provided to turn on/off the heater according to the thermistor settings. Temperature changes can be transmitted as information signals within the analysis tool, and correlated to thermal characteristics of the object under test. Identification or categorisation of the object under test can be performed based on known parameters in a table. It will be appreciated that in addition, or as an alternative, to heat, voltage arc discharge for obtaining characteristics, such as electrical information, may also be performed with the tip sensor.

In an example embodiment, a tip portion can be removably attached to a processing member. Connection members extending from the processing member can electrically connect to a circuitry component of the tip portion through a base cover of the tip portion. The electrical connections from an elongated member such as a tip sensor are then connected to the processing member via electrical connection from the elongated member to the circuitry component. Preferably, calibration can be carried out to calibrate e.g. the sensitivity of the tip sensor.

Figure 8:
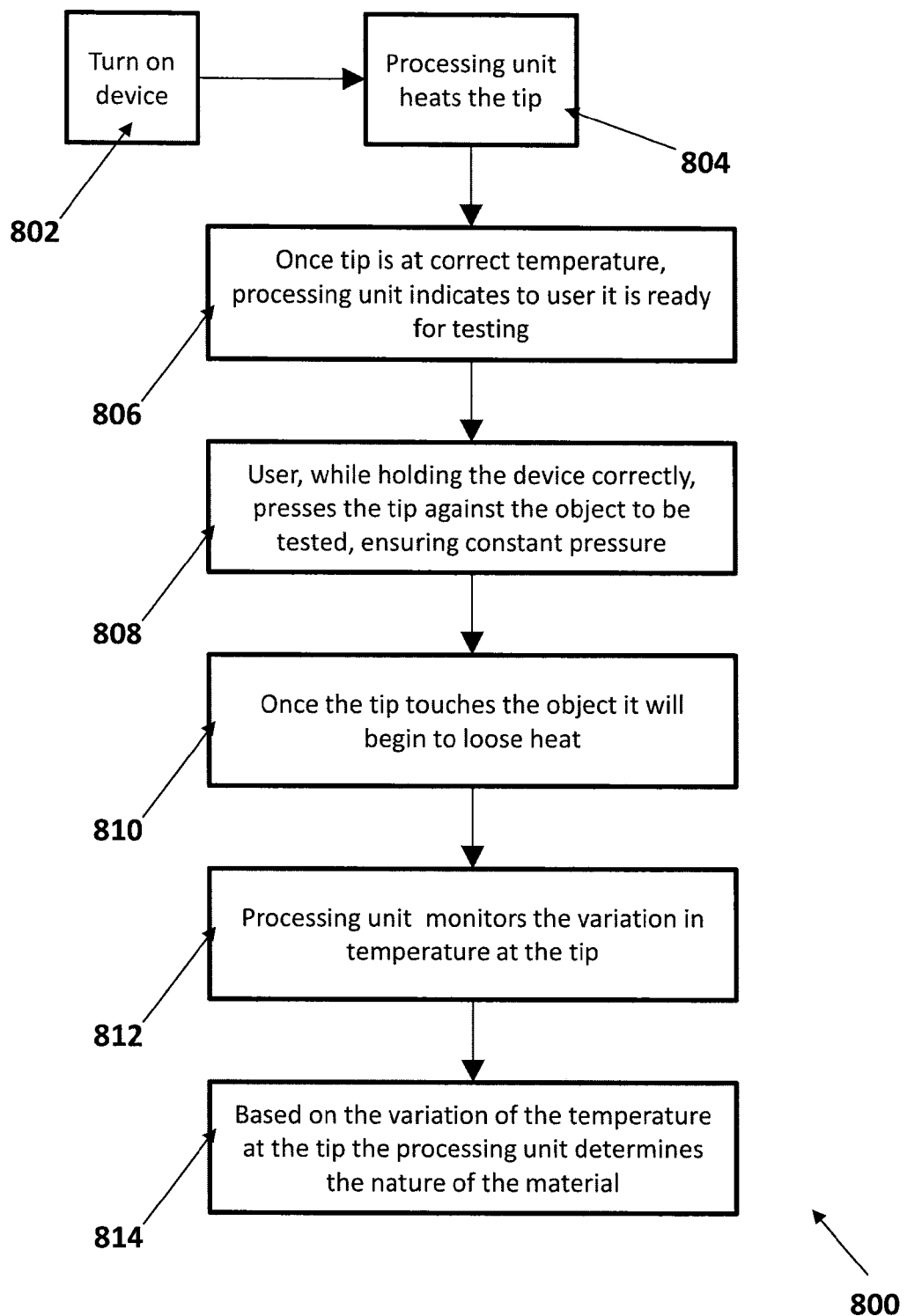
FIG. 8 is a schematic flowchart for illustrating a method of using an analysis tool in an example embodiment.

FIG. 8 is a schematic flowchart 800 for illustrating a method of using an analysis tool in an example embodiment. The analysis tool comprises a detachable member detachably coupled to a separate processing member. At step 802, the analysis tool or device is switched on. At step 804, a processing module/unit e.g. disposed within the processing member activates heating of a probe member such as an elongate or cylindrical rod/tip at the detachable member. The heater is performed using a heater element connected to the tip. At step 806, if it is determined that the tip is at a desired temperature e.g. via feedback from a thermistor connected to the tip, the processing unit provides an indication, e.g. a visual LED light to the user of the analysis tool, to indicate that the analysis tool may be used for testing an object under test. At step 808, the user may contact the tip against the object under test with pressure applied on the tip to ensure desired contact. At step 810, the tip is determined to lose heat upon contact with the object under test. At step 812, the processing unit monitors and determines the variation of temperature (or loss of heat energy) at the tip. This may be performed by converting heat readings into analogue signals using the thermistor. At step 814, the temperature variation is transmitted as information signals within the analysis tool, and based on the variation of temperature, the processing unit determines the nature, or characterises, the object under test. For example, the information signals may be correlated to thermal characteristics of the object under test. Identification or categorisation of the object under test may be performed based on known parameters in a table e.g. stored in an external/internal memory accessible by the processing unit.

Thus, the example embodiment can provide an analysis tool with a detachable member. The analysis tool can be a tester or characteristics reader. Various objects can be analysed including, but not limited to, gemstones such as diamonds, Moissanite, sapphire, metallic/metal stones, as well as other material.

In some embodiments, an additional resilient member such as a spring may be added to the tip portion and coupled to the elongated member. The additional resilient member can be arranged such that upon contact of the elongated member with an object under test or hard surface, a signal is sent to the processing member to switch on for processing. That is, it may be provided that the analysis tool is switched on by simply contacting the tip sensor on a surface.

In some embodiments, a usage sensor may be provided with the processing member. The usage sensor can advise a user on whether the detachable member, or the tip sensor held in the tip sensor holder, is to be replaced. The usage sensor may be a counter that counts the number of times the tip has been heated. The usage sensor may also be a counter that counts the length of time the tip has been electrically powered. A usage sensor may also be additionally or alternatively be provided within the detachable member.

In some embodiments, the contact pads to connection members (such as pogo pins) arrangement can be reversed. That is, the connection members may be provided at the detachable member or tip portion. At the processing member, instead of providing connection members, the connection members may be substituted with contact pads that can electrical connect with connections members from the detachable member.

Further, while it has been described that soldering of wires is performed at e.g. contact pads and e.g. connecting an elongated member to a tip sensor holder, it will be appreciated that other forms of electrically connection may be carried out. For example, plastic wire connectors or mating electrical contacts can be used etc.

In addition, while it has been described that the detachable member and the processing member are connected using contact pads and connector members disposed respectively, it will be appreciated that the description is not limited as such. For example, the detachable member can be electrically connected in a removable manner using any types of connectors such as using universal serial bus (USB) connectors, mini- USB connectors, micro-USB connectors and even wireless transmit-receive connectors etc.

Furthermore, while six connections have been illustrated for the connections from the elongated member, it will be appreciated that the connections are not limited as such, and can include more signal detecting connections such as for providing voltage discharges to objects under test and for receiving voltage readings across the objects under test etc.

In addition, while calibration has been described as being for calibrating the tip sensor, it will be appreciated that other forms of calibration can also be performed. For example, calibration may be carried out to the processing module of the processing member. This may be desired for each software reset or change of power supply etc. For example, the calibration of the tip sensor may be based on preset parameters in a processor/controller or processing module of the processing member, and as such, a firmware update can be performed to the processing module to improve calibration. Thus, the tip sensor can be recalibrated with new parameters with the updating of the firmware.

Furthermore, any description referring to electrical connection methods, such as hard soldering of wires etc., are understood to be not limited as such, and can include other methods of electrical connections including non-permanent forms of connections such as using electrical connectors.

In addition, while the tip portion circuitry component has been described variously in the form of a printed circuit board, the component is not limited as such and can be other forms as long as it fulfils the purpose of providing electrical connections from the components of the tip portion, such as from a tip sensor holder or a tip, to components of a processing member, such as connection members of a connector portion.

Further, while the example embodiments utilise an elongate member as a probe member, it will be appreciated that the probe member is not limited as such. The probe member may assume any shape or size that is suitable for contacting an object under test and for obtaining characteristics information of the object under test for transmission to a processing member. The probe member may thus also be, but not limited to, a cylindrical pillar/rod or a curved member such as a ball shaped conductor.

In some example embodiments, a kit for an analysis tool may be provided whereby the kit comprises a detachable member as described in one or more of the above example embodiments; and a processing member as described in one or more of the above example embodiments.

In some example embodiments, a method for analysing an object may be provided whereby the method comprises providing a detachable member as described in one or more of the above example embodiments; providing a processing member as described in one or more of the above example embodiments; and detachably coupling the detachable member and (or to) the processing member.

It will be appreciated by a person skilled in the art that other variations and/or modifications may be made to the specific embodiments without departing from the spirit or scope of the invention as broadly described. The present embodiments are, therefore, to be considered in all respects to be illustrative and not restrictive.

The invention claimed is:

1. A gemstone analysis tool detachable member, the member comprising,
   a housing for a probe member, said probe member capable of obtaining one or more characteristics information of a gemstone;
   a circuitry component for co-operating with said probe member, the circuitry component comprising one or more electrical connections for transmitting said one or more characteristics information of the gemstone to a separate processing member of a gemstone analysis tool such that said one or more characteristics information of the gemstone is capable of being used by the separate processing member for analysis;
   a base cover engaging the housing and maintaining the probe member and the circuitry component within the housing, the base cover defining one or more openings exposing the one or more electrical connections for contact by the separate processing member; and
   a mating part for detachably coupling the detachable member in mechanical connection to the separate processing member;
   wherein the circuitry component is configured to be removable from electrical communication with the separate processing member;
   and wherein the electrical communication comprises usage of one or more contact pads in cooperation with one or more spring-loaded members.

2. The gemstone analysis tool detachable member as claimed in claim 1, wherein the gemstone analysis tool is a portable gemstone analysis tool.

3. The gemstone analysis tool detachable member as claimed in claim 2, wherein the portable gemstone analysis tool is a hand-held analysis tool.

4. The gemstone analysis tool detachable member as claimed in claim 1, wherein the circuitry component is capable of being electrically coupled to the probe member, said probe member being configured at one contact end for analysis.

5. The gemstone analysis tool detachable member as claimed in claim 1, wherein the circuitry component of the detachable member comprises the one or more contact pads for said electrical communication and the one or more contact pads are configured to be removable from electrical communication with one or more spring loaded members of the separate processing member.

6. The gemstone analysis tool detachable member as claimed in claim 1, comprising said probe member and wherein the probe member comprises a cylindrical rod.

7. The gemstone analysis tool detachable member as claimed in claim 6, wherein the cylindrical rod comprises one or more biasing members for providing a spring action upon contact.

8. The gemstone analysis tool detachable member as claimed in claim 7, wherein the one or more biasing members are arranged to switch on the separate processing member upon contact with a surface.

9. The gemstone analysis tool detachable member as claimed in claim 1, wherein the base cover comprises mating components configured to interlock with complementary mating components on the separate processing member.

10. A gemstone analysis tool processing member, the processing member comprising,
    a mating part to detachably couple the processing member in mechanical connection to a gemstone analysis tool detachable member as claimed in claim 1;
    a connector portion for receiving one or more characteristics information of a gemstone obtained at the gemstone analysis tool detachable member, the connector portion being arranged to be in electrical communication with a processing module for analysis of said one or more characteristics information of the gemstone;

wherein the processing member is capable of being used with an object under test, said object comprising a gemstone; and wherein the connector portion is configured to be in electrical communication and removable from electrical communication with the gemstone analysis tool detachable member;

the connection to the gemstone analysis tool detachable member being via one or more electrical connections for contact at one or more openings defined by a base cover of the detachable member;

wherein the electrical communication comprises usage of one or more contact pads in cooperation with one or more spring-loaded members.

11. The gemstone analysis tool processing member as claimed in claim 10, wherein the gemstone analysis tool is a portable gemstone analysis tool.

12. The gemstone analysis tool processing member as claimed in claim 11, wherein the portable gemstone analysis tool is a hand-held analysis tool.

13. The gemstone analysis tool processing member as claimed in claim 10, wherein the connector portion comprises the one or more spring-loaded members configured for said electrical communication to one or more contact pads of the gemstone analysis tool detachable member.

14. The gemstone analysis tool processing member as claimed in claim 10, further comprising an inner cover for exposing one or more connection points of the connector portion, wherein the inner cover is configured to maintain the connector portion within the processing member.

15. The gemstone analysis tool processing member as claimed in claim 10, further comprising a usage sensor configured to inform a user on replacement of the gemstone analysis tool detachable member.

16. The gemstone analysis tool processing member as claimed in claim 10, wherein the connector portion comprises the one or more contact pads for said removable electrical connection to one or more spring-loaded members of the gemstone analysis tool detachable member.

17. The gemstone analysis tool processing member as claimed in claim 10, wherein said one or more characteristics information of the gemstone is capable of being used by the processing member to determine one or both of a thermal conductivity and an electrical conductivity of the gemstone.

18. The gemstone analysis tool detachable member as claimed in claim 1, wherein the circuitry component of the detachable member comprises the one or more spring-loaded members for said removable electrical communication and the one or more connection members are configured to be in removable electrical communication with one or more contact pads of the separate processing member.

19. The gemstone analysis tool detachable member as claimed in claim 1, wherein said one or more characteristics information of the gemstone is capable of being used by the processing member to determine one or both of a thermal conductivity and an electrical conductivity of the gemstone.

20. A gemstone analysis tool, the analysis tool comprising,
a gemstone analysis tool detachable member;
a separate gemstone analysis tool processing member;
the gemstone analysis tool detachable member comprises,
a housing for a probe member, said probe member capable of obtaining one or more characteristics information of a gemstone;
a circuitry component for co-operating with said probe member, the circuitry component comprising one or more electrical connections for transmitting said one or more characteristics information of the gemstone to the separate gemstone analysis tool processing member such that said one or more characteristics information of the gemstone is capable of being used by the separate processing member for analysis;
a base cover engaging the housing and maintaining the probe member and the circuitry component within the housing, the base cover defining one or more openings exposing the one or more electrical connections for contact by the separate processing member; and
a mating part for detachably coupling the detachable member in mechanical connection to the separate processing member;
wherein the circuitry component is configured to be removable from electrical communication with the separate processing member;
the gemstone analysis tool processing member comprises,
a mating part to detachably couple the processing member in mechanical connection to the gemstone analysis tool detachable member;
a connector portion for receiving said one or more characteristics information of the gemstone obtained at the gemstone analysis tool detachable member, the connector portion being arranged to be in electrical communication with a processing module for analysis of said one or more characteristics information of the gemstone, the connection to the gemstone analysis tool detachable member being via one or more electrical connections for contact at one or more openings defined by a base cover of the detachable member;
wherein the processing member is capable of being used with an object under test, said object comprising a gemstone;
wherein the connector portion is configured to be in removable electrical communication with the gemstone analysis tool detachable member;
further wherein the detachable member is detachably coupled in mechanical connection to the processing member;
wherein the detachable member is configured to be in electrical communication and removable from electrical communication with the processing member, and
wherein the electrical communication comprises usage of one or more contact pads in co-operation with one or more spring-loaded members.

21. The gemstone analysis tool as claimed in claim 20, wherein said one or more characteristics information of the gemstone is capable of being used by the processing member to determine one or both of a thermal conductivity and an electrical conductivity of the gemstone.

22. A method of testing gemstones, the method comprising:
providing a gemstone analysis tool, the gemstone analysis tool comprising a gemstone analysis tool processing member and a first gemstone analysis tool detachable member, the first gemstone analysis tool detachable member including a first base cover engaging a housing of the first detachable member and maintaining a probe member and a circuitry component within the housing, the first base cover defining one or more openings exposing the one or more electrical connections for contact by the gemstone analysis tool processing member, the gemstone analysis tool processing member and the first gemstone analysis tool detachable member being in removable electrical and mechanical connection, the electrical connection between the gemstone analysis tool processing member and the first gemstone analysis tool detachable member comprises usage of one or more contact pads in cooperation with one or more spring-loaded members;

applying the gemstone analysis tool to a gemstone;

providing one or more electrical signals from the first gemstone analysis tool detachable member to the gemstone analysis tool processing member through the electrical connection;

ascertaining from the one or more electrical signals one or more first characteristics information of the gemstone;

detaching the first gemstone analysis tool detachable member from the gemstone analysis tool processing member;

obtaining a second gemstone analysis tool detachable member, the second gemstone analysis tool detachable member including a second base cover engaging a housing of the second detachable member and maintaining a probe member and a circuitry component within the housing, the second base cover defining one or more openings exposing the one or more electrical connections for contact by the gemstone analysis tool processing member;

coupling the second gemstone analysis tool detachable member with the gemstone analysis tool processing member such that the gemstone analysis tool processing member and the second gemstone analysis tool detachable member are in removable electrical and mechanical connection, the electrical connection between the gemstone analysis tool processing member and the second gemstone analysis tool detachable member comprises usage of one or more contact pads in cooperation with one or more spring-loaded members;

applying the gemstone analysis tool to the gemstone;

providing one or more electrical signals from the second gemstone analysis tool detachable member to the gemstone analysis tool processing member through the electrical connection; and ascertaining from the one or more electrical signals one or more second characteristics information of the gemstone.

23. The method of testing gemstones of claim 22, wherein the gemstone analysis tool comprises a usage sensor, the method further comprising:

receiving from the usage sensor an indication that the first gemstone analysis tool detachable member is to be replaced, wherein the detaching, obtaining, and coupling steps are performed in response to the indication.

24. The method of claim 22, wherein coupling the second gemstone analysis tool detachable member with the gemstone analysis tool processing member comprises extending the one or more spring-loaded members through the openings in the second base cover of the second gemstone analysis tool detachable member.

25. The method of claim 22, wherein one of the steps of ascertaining from the one or more electrical signals comprises determining one or both of a thermal conductivity and an electrical conductivity of the gemstone.

* * * * *